US00PP30701P2

(12) United States Plant Patent
Stemkens

(10) Patent No.: US PP30,701 P2
(45) Date of Patent: Jul. 9, 2019

(54) ***SEDUM* PLANT NAMED 'SETZ0001'**

(50) Latin Name: *Sedum spurium*
Varietal Denomination: SETZ0001

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/732,139

(22) Filed: Sep. 22, 2017

(51) Int. Cl.
*A01H 5/02* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 6/328
See application file for complete search history.

*Primary Examiner* — Keith O. Robinson
(74) *Attorney, Agent, or Firm* — Dale Skalla

(57) ABSTRACT

A new *Sedum* plant named 'SETZ0001' particularly distinguished by its compact, dense and well branched mounded habit, with dark glossy leaves and a very deep rose flower color.

1 Drawing Sheet

Latin name of the genus and species of the plant claimed: *Sedum spurium.*

Varietal denomination: 'SETZ0001'.

BACKGROUND OF THE NEW PLANT

The present invention comprises a new *Sedum*, botanically known as *Sedum spurium* and hereinafter referred to by the variety name 'SETZ0001'.

'SETZ0001' is a product of a planned breeding program. The new cultivar 'SETZ0001' has small deep rose inflorescences that are early flowering, a dark green narrow-leaved compact, densely branched mounded plant.

'SETZ0001' originates from an open pollination in a container field in July 2010 in Enkhuizen, The Netherlands. The female parent was an unpatented, proprietary plant designated 'P6138-1' with smaller deep pink flowers, lighter green foliage and is less branched when compared to 'SETZ0001'.

The male parent of 'SETZ0001' was an unknown plant in the container field. The resultant seed was sown in March 2011 in Enkhuizen, The Netherlands.

'SETZ0001' was selected as one flowering plant within the progeny of the stated cross in July 2011 in a container field in Enkhuizen, The Netherlands.

The first act of asexual reproduction of 'SETZ0001' was accomplished when vegetative cuttings were propagated from the initial selection in August 2011 in a greenhouse in Enkhuizen, The Netherlands.

BRIEF SUMMARY OF INVENTION

Horticultural examination of plants grown from cuttings of the plant initiated in March 2017 in Enkhuizen, The Netherlands, and continuing thereafter, has demonstrated that the combination of characteristics as herein disclosed for 'SETZ0001' are firmly fixed and are retained through successive generations of asexual reproduction.

'SETZ0001' has not been observed under all possible environmental conditions. The phenotype may vary significantly with variations in environment such as temperature, light intensity and day length.

A Plant Breeder's Right for this cultivar has not yet been applied for. 'SETZ0001' has not been made publicly available prior to the effective filing date of this application, notwithstanding any disclosure that may have been made less than one year prior to the effective filing date of this application by the inventor or another who obtained 'SETZ0001' directly from the inventor.

The following traits have been repeatedly observed and are determined to be basic characteristics of the new variety. The combination of these characteristics distinguishes this *Sedum* as a new and distinct variety.

BRIEF DESCRIPTION OF THE PHOTOGRAPH

The accompanying photographic drawing shows typical flower and foliage characteristics of 'SETZ0001' with colors being as true as possible with an illustration of this type. The photographic drawing shows in FIG. 1 a flowering plant of the new variety.

DETAILED BOTANICAL DESCRIPTION

The plant descriptions and measurements were taken in Enkhuizen, The Netherlands under natural light in August 2017. These plants were approximately 14 weeks old and were growing in 13 cm pots in container field trials. The plants used for the photographs were about 14 weeks old growing in Enkhuizen, The Netherlands and the photograph was taken in July 2017.

Color Chart used: Royal Horticultural Society Colour Chart (R.H.S.) 2001

TABLE 1

DIFFERENCES BETWEEN THE NEW VARIETY 'SETZ0001' AND A SIMILAR VARIETY

| | SETZ0001' (candidate) | 'Fuldaglut' (Unpatented) |
|---|---|---|
| Branching: | More branches | Less branches |
| Flower color: | Deep rose | Rose |
| Plant habit: | More dense, compact and mounding | More loose plant habit |

Plant:
- *Form, growth and habit.*—Dense, compact, mounded and branched. Branches develop roots when they touch the soil.
- *Plant height.*—14 cm.
- *Plant height* (*inflorescence included*).—15 cm (without pot).
- *Plant width.*—30.0 cm.

Roots:
- *Number of days to initiate roots.*—About 9 days at about 18 degrees C.
- *Number of days to produce a rooted cutting.*—3 weeks at 18 degrees C.
- *Type.*—Fine, fibrous, white, moderate branched.
- *Color.*—RHS N155B but whiter.

Foliage:
- *Arrangement and attachment.*—Alternate simple-decussate, sessile.
- *Immature, leaf color, upper surface.*—RHS 144C.
- *Lower surface.*—RHS 144B.
- *Mature, leaf color, upper surface.*—RHS 144C.
- *Lower surface.*—RHS 144B.
- *Length.*—1.5 (juvenile)-1.8 (adult) cm.
- *Width.*—1.2 (juvenile)-1.4 (adult) cm.
- *Shape.*—Acicular.
- *Base shape.*—Truncate.
- *Apex shape.*—Acute.
- *Margin.*—Entire.
- *Orientation.*—Ascending.
- *Texture, upper surface.*—Glabrous and waxy.
- *Lower surface.*—Glabrous and waxy.
- *Color of veins, upper surface.*—RHS 144B.
- *Color of veins, lower surface.*—RHS 144B.
- *Venation pattern.*—Not conspicious.
- *Petiole.*—Not existing: Sessile.

Stem:
- *Habit.*—Round.
- *Quantity of main branches.*—About 2-5, with each many lateral branches.
- *Color of stem.*—RHS 146D and upper side turning purple: RHS 144C.
- *Length of stem.*—15-20 cm.
- *Diameter.*—0.6 cm.
- *Length of internodes.*—1-1.8 cm.
- *Texture.*—Smooth.

Inflorescence:
- *Type.*—Terminal, cymose, drooping.
- *Quantity of inflorescences per plant.*—20-40.
- *Inflorescence length.*—4-5 cm.
- *Inflorescence width.*—3-3.5 cm at widest point.
- *Lastingness of individual blooms on the plant.*—About 8 days.
- *Fragrance.*—None.

Bud (just before opening/showing color):
- *Color.*—RHS 63D.
- *Length.*—0.3 cm.
- *Width.*—0.3 cm.
- *Shape.*—Perfect conical.
- *Pedicel color.*—RHS 186D.
- *Pedicel length.*—0.4 cm.
- *Pedicel diameter.*—0.4 cm.
- *Pedicel texture.*—Smooth.

Peduncle:
- *Shape.*—Round.
- *Length.*—1.2 cm.
- *Width.*—0.3 cm.
- *Color.*—144C.
- *Texture.*—Glabrous.

Flower:
- *Number of flowers per inflorescence.*—80-90.
- *Number of petals.*—5.
- *Petal, length.*—0.3-0.5 cm.
- *Petal, width.*—0.2-0.3 cm.
- *Floret depth.*—0.6 cm.
- *Flower depth.*—0.4 cm.
- *Petal color, upper surface.*—RHS 65D.
- *Lower surface.*—RHS 65C.
- *Shape.*—Ovate to lanceolate.
- *Base.*—Truncate.
- *Apex shape.*—Acute.
- *Margin.*—Entire.
- *Petal texture, upper surface.*—Glabrous.
- *Lower surface.*—Glabrous.
- *Flower fragrance.*—None.

Pedicel:
- *Shape.*—Round.
- *Length.*—0.4 cm.
- *Width.*—0.3 cm.
- *Color.*—RHS 187D.
- *Texture.*—Smooth.

Sepals:
- *Quantity.*—5 sepals.
- *Color, upper surface.*—RHS 144B.
- *Lower surface.*—RHS 144B.
- *Length.*—0.25 cm.
- *Width.*—0.2 cm.
- *Shape.*—Ovate to lanceolate.
- *Apex shape.*—Acute.
- *Base.*—Truncate.
- *Margins.*—Entire.
- *Texture, upper/inner surface.*—Glabrous.
- *Lower/outer surface.*—Glabrous.

Reproductive organs:
- *Gynoecium.*—
- *Pistil quantity.*—5.
- *Length.*—0.1-0.4 cm.
- *Style shape.*—Lanceolate.
- *Style color.*—144C.
- *Style length.*—0.25-0.3 cm.
- *Stigma color.*—151B.
- *Stigma shape.*—Globose.
- *Ovary length.*—0.2 cm.
- *Ovary color.*—RHS 186B.
- *Androecium.*—
- *Stamens, quantity.*—10.
- *Color of filaments.*—RHS 145D-RHS 184A.
- *Length of filaments.*—0.2-0.3 cm.
- *Anther color.*—RHS 154D.

*Anther length*.—0.05 cm.
*Anther shape*.—Oval.
*Color of pollen*.—RHS 151C.
*Pollen amount*.—Sparse.
*Fruit*.—
*Shape*.—Rounded with pointed tip.
*Length*.—0.2 cm.
*Width*.—0.15 cm.
*Color*.—RHS186C.
*Disease/pest resistance*.—Was not observed.

What is claimed is:

1. A new and distinct variety of *Sedum spurium* plant named 'SETZ0001' substantially as illustrated and described herein.

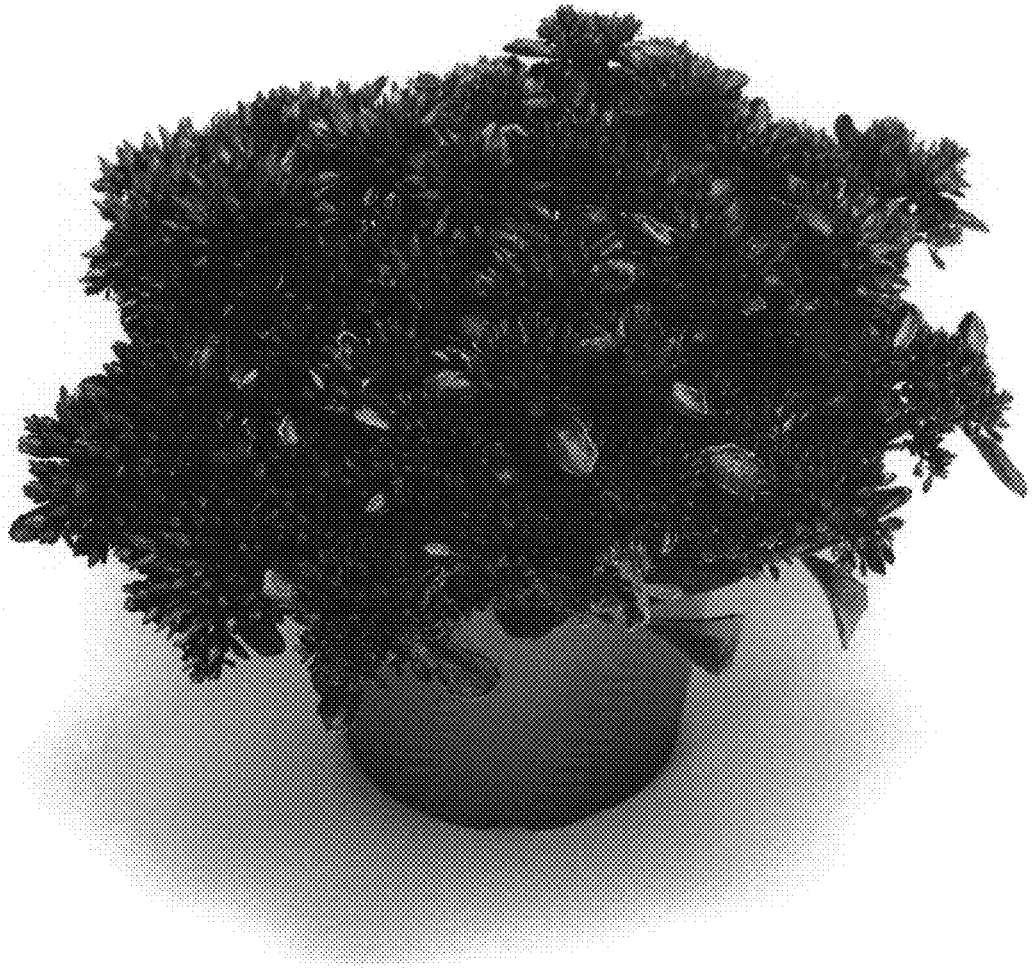

* * * * *